United States Patent [19]  [11] 4,257,938
Hosoi et al.  [45] Mar. 24, 1981

[54] PURIFICATION METHOD OF HUMAN FIBROBLAST INTERFERON

[75] Inventors: Kazuo Hosoi, Kamakura; Hitoshi Ozawa, Hiratsuka, both of Japan

[73] Assignee: Toray Industries, Inc., Tokyo, Japan

[21] Appl. No.: 89,165

[22] Filed: Oct. 29, 1979

[30] Foreign Application Priority Data

Nov. 7, 1978 [JP] Japan .................................. 53-137035

[51] Int. Cl.³ ............................................. B01D 15/00
[52] U.S. Cl. .................................. 260/112 R; 210/656; 210/691; 210/908; 210/927; 424/85
[58] Field of Search ............... 210/24, 32, 31 R, 31 C, 210/36, 40; 260/112 R; 424/85; 435/68, 272, 811

[56] References Cited

U.S. PATENT DOCUMENTS

| 3,144,390 | 8/1964 | Burke | 424/85 |
| 3,265,581 | 8/1966 | Fantes et al. | 424/85 |
| 3,414,651 | 12/1968 | Fantes | 424/85 |
| 3,975,344 | 8/1976 | Schwartz | 424/85 |
| 4,168,261 | 9/1979 | Edy | 424/85 |

FOREIGN PATENT DOCUMENTS 7605805 11/1977 Netherlands ............................. 424/85

Primary Examiner—Ivars C. Cintins
Attorney, Agent, or Firm—Miller & Prestia

[57] ABSTRACT

A method for the purification of human fibroblast interferon by the successive treatments of a crude interferon solution with a strongly acidic ion exchanger and a chelating carrier which contains a chelating residue chelated with at least one metal ion selected from the group consisting of $Co^{++}$, $Ni^{++}$, $Zn^{++}$, and $Cu^{++}$.

14 Claims, No Drawings

PURIFICATION METHOD OF HUMAN FIBROBLAST INTERFERON

This invention relates to a method for the purification of interferon. Interferon is a protein having antiviral activity which is produced by living cells when they are stimulated by viruses or by other specific chemical reagents.

When an animal tissue or cell is treated with interferon, the tissue or cell becomes resistant to infection by various viruses (antiviral state). Infection by wide ranges of viruses can be prevented by the antiviral state and, in this sense, interferon is virus-nonspecific. On the other hand, interferon has species or origin specificity. The cells of one species can attain an antiviral state only when the cells are treated with an interferon originated from the same species. The action of interferon is profound and is not restricted to antiviral activity. It has been reported that it has potential antitumor activity, inhibitory activity toward cell growth, activation of macrophage activity, etc.

For these reasons, interferon is expected to be a promising medicament not only for the treatment and prophylaxis of viral diseases but also for treatment of cancerous conditions such as osteosarcoma or leukemia, for example.

Due to the specificity of the species, the interferon used for therapeutic purposes should be human interferon which is produced by human cells.

This invention relates to a method for the purification of human interferon. There are at least two kinds of human interferon. One has L-type immunogenicity and is produced by human lymphocyte cells or by other lined cells, such as Namalva cells, so it is called L-interferon. The other has F-type immunogenicity and is produced by human fibroblast cells or by other lined cells, such as MG-63 cells, so it is called F-interferon.

More specifically, this invention relates to F-interferon and especially to the concentration and purification of crude F-interferon.

F-interferon can be produced from fibroblast cells which are cultured on a glass surface, a suitable plastic surface, or on beads such as DEAE-Sephadex. The cells are treated with double strandard RNA (for example, Poly I:Poly C) and then with cycloheximide and actinomycin D, by which induction procedures the cells start the production of interferon for a subsequent 20 to 48 hours. The Eagle MEM medium (if necessary, enriched with serum) is usually used for the production of interferon; however, other nutrients or additives may be added. The crude interferon solution thus obtained contains a very small amount of interferon ($10^3-10^5$ IU/ml $= 10^{-6}-10^{-4}$ mg/ml) and many impurities originating from the culture medium and the cells. Consequently, the concentration and purification of the crude preparation is a prerequisite to its use for therapeutic purposes. Until the time the present invention was made, no one is believed to have obtained pure F-interferon. Pure F-interferon is believed to have a specific activity of about $10^9$ IU/mg protein.

Numerous methods have been reported for the purification of F-interferon preparations. For the purpose of partial concentration and purification, precipitation methods were employed, for example those using ammonium sulfate. Ultrafiltration was used in some cases. Ion exchange chromatography was also used, for example by employing CM-Sephadex chromatography. Gel chromatography was used for purification and desalination (Sephadex G-100, G-25 etc.).

Recently, hydrophobic chromatography was reported as being successful for the purification of various interferons. For such a purpose, concanavalin-A-, octyl-, tryptophyl-, or phenyl-agarose were used. [W. A. Carter et al, J. Biol. Chem., 251, 5381, (1976); ibid., 251, 7260 (1976); Biochemistry, 15, 704 (1976)]. Polynucleotide affinity chromatography was applied by Stewart et al, [W. E. Steward II, et al, Interferon Scientific Memorandum I-A, 562 (1978)]. Immune chromatography was also used as disclosed by Berg et al, [K. Berg et al, Scand. J. Immunology, 8, 429 (1978)]. Chromatography on a controlled pore glass was disclosed by Edy et al. [V. G. Edy et al, J. Gen. Vivol., 33, 517 (1976)].

Edy et al also reported the use of zinc chelate chromatography for the purification of F-interferon [V. G. Edy et al, J. Biol. Chem., 252, 5934 (1978)]. As disclosed by Edy et al, about 14 times the column volume of the original interferon solution (pH 7.4) was added to a column containing a zinc chelate carrier. After elution with an acidic solution F-interferon was obtained which was purified 32 times. When elution was performed using the pH gradient elution method, 3100 times purification was achieved and there was obtained a purified preparation having a specific activity of $10^{8.5}$ IU/mg protein. This chromatographic system seems good but still has shortcomings when dealing with a large quantity of interferon solution and for obtaining a drug preparation which is applicable for human use. Judging from the results, the elution profile of interferon was lacking in sharpness and a rather large volume of eluant was needed. Consequently, the interferon titer of recovered solution was not very high (about $1.1-2 \times 10^5$ IU/ml), and the salt concentration of the recovered solution was about 6 times higher than that of physiological fluid.

Copper chelate chromatography of F-interferon was reported by Sulkowsky et al [J. Gen. Virology, 43, 701, (1979)], but in that case, the recovery of interferon from the column was low and appeared to be impractical.

An object of this invention is to provide an economic purification method for human F-interferon which can be applicable for use with a large quantity of crude interferon solution and to provide a highly purified and highly concentrated interferon preparation with appreciable recovery.

From these standpoints, we have reexamined the above mentioned zinc chelate affinity chromatography, especially giving attention to the capacity of F-interferon for the zinc chelate column as follows:

A crude F-interferon solution (50 times the column volume) produced by human fibroblast cell in an Eagle-MEM medium was passed through a zinc chelate column. F-interferon activity was absorbed and eluted almost quantitatively. However, when the charge volume was increased to 150 times the column volume, almost 100% of the interferon activity passed through the column and was found in the effluent. This result indicated that one volume of a zinc chelate column can absorb only the F-interferon present in less than 150 volumes of the original solution.

If it is desired to apply zinc chelate chromatography directly to the purification of a crude F-interferon solution, it becomes necessary to use a large volume of zinc chelate carrier, which is rather expensive, for the handling of a large volume of original solution. The use of a large column results in the inevitable decrease in purity (nonspecific absorption of protein) and in concentration of the recovered interferon solution.

It is a further object of this invention to provide a novel method for the purification of human F-interferon which overcomes the aforementioned disadvantages.

It has now been discovered that the foregoing disadvantages may be overcome by utilizing an entirely novel procedure. A crude F-interferon solution produced by human cells is treated with a strongly acidic ion exchanger under acidic conditions. The interferon absorbed on the ion exchanger is eluted with an eluant. The recovered F-interferon solution is then treated with a transition metal chelate carrier. The interferon absorbed on the metal chelate carrier is detached from the carrier to give a highly purified and highly concentrated F-interferon preparation. According to this invention, the capacity of the metal chelate carrier becomes so high that one volume of the carrier can absorb almost all of the F-interferon activity which is originally present in about 1,000–6,000 volumes of the crude F-interferon solution.

The crude F-interferon solution which is used in this invention is produced by human fibroblast cells or established cell lines, such as MG-63. These cells are cultured on a glass or plastic surface and are treated with an interferon inducer, such as Poly I:Poly C, and with some other super inducers, for example, cycloheximide and actinomycin D. The cells begin to produce F-interferon in the culture medium and continue production for the following 20–48 hours. The culture medium containing F-interferon is collected and used as the crude and original F-interferon solution.

For the culture medium of the interferon production, an Eagle-MEM solution may be used and, if necessary, serum or other additives can be included. Other media, such as an Earle's medium, etc., can also be used.

The strongly acidic ion exchangers used in this invention are water-insoluble polysaccharide derivatives or polyolefin derivatives to which a sulfonyl group is introduced. Preferably, water-insoluble polysaccharide derivatives having a sulfonyl group are used. Even more preferable, cross-linked dextran derivatives are used, for example, "SP-Sephadex". Both Na+ type and H+ type of strongly acidic ion exchangers can be used in this invention. For the contacting of the strongly acidic ion exchangers with interferon, either a batchwise method or a columnwise method can be used, but the latter is preferable.

It is necessary that the interferon solution is made acidic before the absorption of F-interferon on the ion exchanger occurs, preferably, a pH between 1 and 3. When some insoluble materials are observed in the original acidified interferon solution, it is preferable to remove the insoluble materials either by centrifugation or by filtration.

The contact of the crude interferon solution with a strongly acidic ion exchanger is continued until practically all of the interferon activity is absorbed on the ion exchanger. In the case of column chromatography, a space velocity of 1–10 $hr^{-1}$ is preferred. A sufficient amount of the ion exchanger should be used which would absorb most of the interferon activity. After the completion of absorption, the strongly acidic ion exchanger is washed with sufficient water or acidic solution (pH below 5) to remove the remaining crude interferon solution on the column. A portion of any pyrogenic substances present is removed during this absorption step.

For the recovery of interferon activity from the ion exchanger, suitable buffer solutions at a pH of 5–11 may be used. However, buffer solutions of pH 7–10 are more preferable. For such solutions, phosphate buffer solutions, solutions of basic compounds, with or without an alkali metal chloride, are recommended. Other solutions which are capable of eluting interferon activity from the ion exchanger can also be used. The concentration of buffer solution used for the elution is preferably between 0.01–1 M. The volume and velocity of the eluant used for the elution of interferon from the ion exchanger are usually 1–10 times the volume of the ion exchanger, and with a space velocity (SV) of 1–10 $hr^{-1}$, respectively.

The metal chelate carriers which are used in this invention are polysaccharides or cross-linked polyolefin derivatives, which have chelating groups, such as a biscarboxymethyl amino group, and a transition metal ion bound to the chelating group. Preferably, insoluble polysaccharide derivatives having a chelating group such as a biscarboxymethyl amino group and a transition metal ion chelated thereto is used. For example, the following carrier which was reported by Porath et al [Nature, 258, 598 (1975)] is applicable for this purpose:

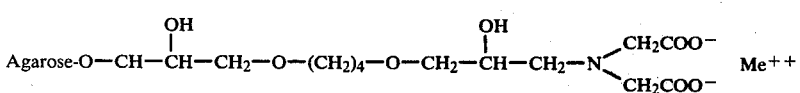

This carrier can be synthesized by reacting an epoxy-activated "Sepharose" (Pharmacia Co.) with iminodiacetic acid. The chelating capacity of the carrier is about 15–20 μmoles/ml of the wet carrier when a commercially available epoxy-activated "Sehparose" is used, but other carriers which have different chelating capacities are also acceptable. This carrier binds a transition metal ion when it is in contact with a solution of the transition metal salt. Washing with water or a saline solution before use is recommended.

The transition metal ions which are used in this invention comprise at least one metal ion selected from the group consisting of $Co^{++}$, $Ni^{++}$, $Zn^{++}$, and $Cu^{++}$. The pH at which the metal chelate carrier makes contact with the recovered solution of the aformentioned ion exchanger is between 6–10. Preferably, a pH of 7–9 is utilized. When the pH of the recovered solution from the strongly acidic ion exchanger is not within this range, adjustment of the pH by an addition of an acid or alkali is recommended. Both batchwise and columnwise methods are of course applicable for this absorption step, but the latter is preferred. After abosrption of the interferon, washing the carrier with water or with a salt solution (pH 6–10) is recommended. This passing through and washing removes many impurities, including pyrogenic substances, if any.

The elution of human fibroblast interferon from the metal chelate carrier, is performed either with an acid solution or a solution of chelating reagents. As the acid solution, a solution of an organic acid, inorganic acid, salt of an organic acid, salt of inorganic acid, or a mixture thereof can be used. The pH of the acid solution is about 2 to about 5.5. For such a solution, an acetic acid-sodium acetate buffer solution, citric acid-sodium phosphate buffer solution, potassium chloride-hydrochloric acid buffer solution, glycine-hydrochloric acid buffer solution, etc., can be named. The concentration of this eluant is preferably about 0.01–1 M. The concentration has some relations to the elution activity so that it is recommended that the elution is continued until practically all of the interferon activity is eluted from the carrier. Another method of elution is through the use of a solution of a chelating reagent. Chelating reagents which may be used include EDTA, histidine, imino diacetic acid, etc., which are known to have chelating activity towards transition metal ions. When considering the toxicity of the chelating agent and its contamination of the final interferon preparation, histidine is considered as one of the more preferable reagents to be used. In the use of the histidine solution, both a solution of histidine hydrochloride and histidine itself can be used. A high concentration of the chelating agent is preferable, so long as it remains in solution.

Generally, interferon can be eluted from the carrier in higher concentration and recovered with a smaller volume of eluant when the chelating reagent is used as the eluant. This is especially true when copper chelate chromatography is applied in the purification of human F-interferon.

The process of the present invention can be generally practiced according to the following.

A. Preparation of crude interferon

Cultivated human fibroblast cells are treated with Poly I:Poly C, and the production of interferon is started (induction step). The cells are treated with cycloheximide and actinomycin D successively (super induction step) and the medium is replaced with a new Eagle-MEM medium. After a 20–48 hours production, the medium is collected and used as the crude interferon solution.

B. Purification of crude interferon solution

All the following purification procedures are performed between 0° C. and room temperature, preferably between 4°–10° C.

The pH of the crude interferon solution is lowered to 1–3 by the addition of hydrochloric acid, and the solution is then passed through a SP-Sephadex column. The amount of the SP-Sephadex used depends in part on the composition of the crude solution, but when the crude solution has an interferon titer of $10^3–2\times10^4$ IU/ml and a protein concentration of 20–50 μg/ml, about 100–500 column volume of the crude solution can be charged at a flow rate of $SV=1–10$ $hr^{-1}$. The column is then washed with a water or acid solution. By means of this chromatography, a part of the contaminated protein and the pyrogenic substances present can be removed (The crude interferon solution frequently contains pyrogenic substances even when cultivation of cells and production of interferon is performed under strictly sterile conditions using pyrogen-free materials and apparatus. Therefore, the nature and behavior of the pyrogenic substance present is different from the typical pyrogen such as the bacterial lipopoly-saccharide). The interferon which is absorbed on the SP-Sephadex is eluted with a weakly basic buffer solution, for example 0.1 M sodium phosphate buffer solution at a pH of 8.5.

A ten column volume of elution is adequate. The eluant from the SP-Sephadex column is then charged to an iminodiacetic acid carrier column, which is chelated with $Co^{++}$, $Ni^{++}$, $Zn^{++}$, or $Cu^{++}$, or a mixture of these metallic ions. The charging may be performed either by passing the pooled eluant from the SP-Sephadex or by passing the eluant of the SP-Sephadex column directly connected to the chelate column. The pH of the charging solution is adjusted to a pH of 6–10, preferably, 7–9, either batchwise or flowwise. The amount of the metal chelate carrier necessary for the complete absorption of interferon activity depends somewhat upon the composition of the eluant of SP-Sephadex, but when the charging and elution of SP-Sephadex is performed with 200–300 and a 10 column volume of crude solution and eluant, respectively, about a one-fifth to about a one-twentieth column volume of SP-Sephadex column is sufficient. Consequently, it is calculated that about 1,000–6,000 times volume of crude interferon solution can be handled with one volume of metal chelate carrier. The metal chelate carrier column is then washed with either water, saline solution or an appropriate buffer solution. During this washing procedure, a large portion of the contaminated protein and the pyrogenic substances which still remain in the interferon fraction can be removed. The column is then eluted with a proper eluant, for example, a 2–5 column volume of 0.2 M histidine solution at pH 7, or 0.1 M sodium phosphate solution at pH 4.5 containing sodium chloride.

C. Preparation and purification of human F-interferon

To the highly concentrated and highly purified interferon solution thus obtained in step B is added human serum albumin for stabilization and the salt or metal ion is removed either by dialysis against water or a dilute salt solution or by Gel-chromatography, for example on "Sephadex" G-25. The desalinated interferon solution is, after aseptic filtration, liophillized to yield an interferon preparation which is suitable for intramuscular or intravenous injection. Some additives, which are effective for the stabilization of interferon may be added.

The merit of the purification method of this invention is more clearly understood when the result of this invention is compared with a method which provides for the separate use of metal chelate chromatography or SP-Sephadex chromatography, respectively. As shown in the following Reference Examples 1 and 2, when a 50 column volume of crude interferon solution is applied to metal chelated columns of $Co^{++}$, $Ni^{++}$, $Zn^{++}$ or $Cu^{++}$, interferon activity is retained on the column and nearly quantitative elution could be achieved by the elution with a histidine solution. However, when the charge volume was increased to 150 columns volume (3 times that of Reference Example 1), most of the interferon activity could not be retained on these columns and the activity was found in the passed-through fractions. The column retained less than 10% of the applied interferon activity.

The experiments show that in the crude interferon solution there are some components which have a higher affinity towards the metal chelate column so that, when the interferon absorbed on the column is replaced by these components, there is an apparent decrease in the capacity of metal chelate carrier towards the interferon solution. The capacity of the metal chelate carrier towards the crude interferon solution is less than 150 times its volume and therefore, unsuitable for any practical purpose.

In the case of "SP-Sephadex" chromatography, the capacity of the ion exchanger is sufficient for the crude interferon solution (more than 300 times the column volume when Eagle-MEM medium is used for the production), and the recovery of interferon activity from the column is satisfactory. However, when interferon is not eluted with a sharp peak, it is necessary to use a large volume of eluant. Consequently, the concentration of interferon in the eluate is not very high (about 10–50 times the concentration). The degree of purification is also not very satisfactory (about $10^6$–$10^7$ IU/mg protein) and the removal of the pyrogenic substances is unsatisfactory so as to result in a critical defect for its use as an injectable.

The results of this invention show that when the partially purified interferon solution by "SP-Sephadex" column treatment was applied to the metal chelate column, the capacity of the column increased markedly and one volume of the metal chelate carrier could absorb interferon which was originally contained in 1,000–6,000 volumes of the crude interferon solution. The elution profile of the interferon from the metal chelate column was very sharp, especially when the elution was performed with a histidine solution. Consequently, it was easy to obtain a highly concentrated and highly purified interferon solution with appreciably high recovery. In addition, significant portions of the contaminated protein and the pyrogenic substances which could not be removed by the SP-Sephadex chromatography were removed during the metal chelate chromatography, whereby a highly useful injectable interferon preparation was obtained.

Apparently, the main reason why the "SP-Sephadex" chromatography resulted in the increase of the capacity of the metal chelate carrier was that certain interfering substances were present in the original interferon solution, which appeared to interfere with the absorption of interferon on the metal chelate carrier, but which were unexpectedly removed by the SP-Sephadex chromatography.

The following Examples serve further to illustrate the invention, but are not intended to define or to limit the scope of the invention, which is defined in the appended claims.

EXAMPLE 1

A crude interferon solution used was prepared by treating human fibroblast cells (normal diploid cell) in an Eagle-MEM medium with Poly I:Poly C and then treating with cycloheximide and actinomycin D (super induction). The crude solution (pH 7.4) which had an interferon activity of 3200 IU/ml and 20 $\mu$g of protein per ml (specific activity, $1.6 \times 10^5$ IU/mg protein) was adjusted to pH 2.0 by the addition of hydrochloric acid and charged on a column of SP-Sephadex (200 ml, 4.6 cm $\times$ 12 cm). After loading 60 l of crude solution (total interferon activity, $1.9 \times 10^8$ IU), the column was washed with 2 l of water. The eluant contained $9.5 \times 10^6$ IU (5%) of interferon activity. The column was then washed with 0.1 M sodium phosphate buffer at pH 8.3 and the interferon was recovered in the first 2.28 l of effluent. This fraction contained $1.8 \times 10^8$ IU (94%) of interferon activity and 23 mg of protein. The specific activity was $8 \times 10^6$ IU/mg protein; 26 times concentration and 50 times purification was achieved.

The carrier for the metal chelate chromatography was prepared by the method of Porath. Iminodiacetic acid (14 g) and sodium carbonate (20 g) was dissolved in water (100 ml), and reacted with an epoxy-activated Sepharose 6B (135 ml, wet volume) for 16 hours at 56° C. After filtration and washing, the carrier was treated with 1 M ethanolamine solution (100 ml) for 4 hours at 56° C., filtered, washed and then stored at 4° C.

A zinc chelate chromatography column (45 ml, 3 cm $\times$ 6.4 cm) was prepared by passing 1% zinc chloride solution on the carrier column. To this column, the effluent from SP-Sephadex column (2.28 l) was loaded and washed with 800 ml of physiological saline solution. The solution which was passed through and the wash solution contained $8 \times 10^6$ IU (4%) of interferon activity. The column was then washed with 0.1 M sodium phosphate buffer solution (pH 4.5) containing physiological saline (1.9, v/v). The first fraction (262 ml) contained $1.4 \times 10^8$ IU (72%) of interferon activity. The concentration of interferon in this fraction was $5.3 \times 10^5$ U/ml and protein was 2 $\mu$g/ml, with a specific activity of $2.7 \times 10^8$ IU/mg protein, which means that 1,700 times purification and 166 times concentration was achieved from the original solution. The crude interferon solution contained pyrogenic substances and was positive toward a Limulus test. Part of the pyrogenic substances passed the "SP-Sephadex" column but the recovered interferon fraction was again positive to a Limulus test. However, the remaining pyrogenic substances were not retained on the zinc chelate column and removed during the charging and washing steps. The effluent from the metal chelate column contained very small amounts of pyrogenic substances. A part of the final effluent, after filtration through a 0.2$\mu$ filter, was injected intravenously into three rabbits ($1.5 \times 10^5$ IU/Kg body weight). The summation of pyroxia of these three rabbits was 0.63° C., which cleared the "Requirement for the Biological Substances, Japan".

EXAMPLE 2

A crude interferon solution similar to that used in Example 1 was used in this experiment. The acidified crude solution (48 l containing 5,000 IU/ml (total activity, $2.4 \times 10^8$ IU) and 25 $\mu$g/ml of protein, was charged on a 200 ml of "SP-Sephadex" column and the column was washed with 2 l of water. The column was then eluted with 2.0 l of a phosphate buffer (0.1 M pH 8.3). $2 \times 10^8$ IU (83%) of interferon activity and 100 mg (10.4%) of protein was recovered (20 times concentration and 10 times purification).

A part of the effluent from "SP-Sephadex" column (200 ml, total interferon activity $2 \times 10^7$, total protein 10 mg) was charged on a 2 ml column of cobalt chelate carrier at a flow rate of 8 ml/hour. After washing with 20 ml each of water and saline, the column was eluted with 0.2 M of histidine solution containing 0.2 M of sodium chloride (pH 7.5). The effluent (6.0 ml) had an interferon activity of $2.3 \times 10^6$ IU/ml (total activity, $13.8 \times 10^6$ IU, 69%) and a protein concentration of 15 g/ml (total protein, 0.09 mg, 0.9% recovery). The specific activity of this fraction was $1.5 \times 10^8$ IU/mg protein and 460 times concentration and 750 times purification was achieved from the crude interferon solution.

EXAMPLE 3

The procedure of Example 2 was followed except that a nickel chelate column was used instead of a cobalt chelate column.

The effluent (6.0 ml) had 2.3×10⁶ IU/ml (recovery, 69%) and 50 μg/ml of protein (recovery 3%). The specific activity was 5×10⁷ IU/mg protein.

EXAMPLE 4

The procedure of Example 2 was followed except that a zinc chelate column was used instead of a cobalt chelate column.

The effluent (6.0 ml) had 2.3×10⁶ IU/ml (recovery 69%) and 30 μg/ml of protein (recovery 1.8%). The specific activity was 8×10⁷ IU/mg protein.

EXAMPLE 5

The procedure of Example 2 was followed except that a copper chelate column was used instead of a cobalt chelate column.

The effluent (6.0 ml) had 1.8×10⁶ IU/ml (recovery 54%) and 150 μg/ml of protein (recovery 9%). The specific activity was 1.2×10⁷ IU/mg protein.

REFERENCE EXAMPLE 1

A crude interferon solution was prepared according to the procedure of Example 1. This solution had an interferon activity of 8,000 IU/ml and a protein concentration of 40 μg/ml. The specific activity was 2×10⁵ IU/mg protein.

Four metal chelate columns (2.0 ml, 0.7 cm×5.2 cm) were prepared, each of which were bound with a cobalt, nickle, copper and zinc ion, respectively.

To these columns, 100 ml of the crude interferon solution (total interferon activity 8×10⁵ IU, total protein 4 mg) was charged at a rate of 8 ml/hour and washed with 20 ml of saline. The columns were then eluted with a 0.2 M histidine solution containing 0.2 M sodium chloride (pH 7.3). The results were as summarized in Table 1, Column A.

In another experiment, the elution of these columns was performed using a 0.2 M acetate buffer solution containing 0.2 M sodium chloride as the eluant (pH 4.0). The results are summarized in Table 1, Column B.

TABLE 1

| | Metal Chelate Chromatography of Crude Interferon Solution* | | | | | | | |
|---|---|---|---|---|---|---|---|---|
| Chelate Metal | $CO^{++}$ | | $Ni^{++}$ | | $Cu^{++}$ | | $Zn^{++}$ | |
| Eluant | A** | B*** | A | B | A | B | A | B |
| IF Activity Charging & Washing | 5% | 5% | 5% | 4% | 3% | 4% | 3% | 3% |
| Effluent (6.0 ml) | 90% | 18% | 100% | 40% | 65% | 0.2% | 100% | 88% |

*Crude interferon solution had 8,000 IU/ml and 40 ug/ml of protein. 100 ml of IF (Interferon) solution was charged to 2.0 ml metal chelate column.
**0.2M Histidine + 0.2 M NaCl (pH 7.3).
***0.2M Acetate buffer + 0.2 M NaCl (pH 4.0).

All the figures in the Table are expressed as the percentage of activity in each fraction to the total activity charged.

REFERENCE EXAMPLE 2

The procedure of Reference Example 1 was followed except that 300 ml of crude interferon solution was charged to each 2.0 ml of metal chelate column to check the capacity of the carrier.

Almost all interferon activity was not retained in the four columns and 80-100% of charged activity was found in the passed-through fractions. Less than 10% of interferon activity was recovered from the column when the column was eluted with a histidine solution or an acidic buffer solution.

We claim:

1. In a method of purifying human fibroblast interferon, the steps which comprise successively
   (a) absorbing an acidified solution of crude human fibroblast interferon upon a strongly acidic ion exchanger,
   (b) contacting the ion exchanger with an eluant which is substantially neutral or weakly basic for a time sufficient to produce an effluent containing the interferon,
   (c) contacting said effluent with a carrier having a chelating residue and including at least one metal ion selected from the group consisting of $Co^{++}$, $Ni^{++}$, $Zn^{++}$, and $Cu^{++}$, wherein said metal ion is chelated to the chelating residue so as to absorb the interferon, and
   (d) contacting said carrier with an eluant for a time sufficient to produce a purified and concentrated interferon solution.

2. The method according to claim 1, wherein said strongly acidic ion exchanger is a water insoluble polysaccharide derivative containing a sulfonyl group.

3. The method according to claim 2, wherein said water insoluble polysaccharide derivative is a cross-linked dextran.

4. The method according to claim 1, wherein said carrier is a water-insoluble polysaccharide derivative having a chelating residue.

5. The method according to claim 1, wherein said carrier is an agarose derivative containing a biscarboxymethylamino group.

6. The method according to claim 1, wherein said strongly acidic ion exchanger is a water insoluble polysaccharide derivative containing a sulfonyl group, and said carrier is a water insoluble polysaccharide derivative containing a chelating residue.

7. The method according to claim 1, wherein said strongly acidic ion exchange is a cross-linked dextran containing a sulfonyl group, and said carrier is an agarose compound containing a biscarboxymethylamino group.

8. The method according to claim 1, wherein said metal ion is $Co^{++}$.

9. The method according to claim 1, wherein said metal ion is $Ni^{++}$.

10. The method according to claim 1, wherein said metal ion is $Cu^{++}$.

11. The method according to claim 1, wherein said metal ion is $Zn^{++}$.

12. The method according to claim 1, wherein said eluant contacted with the carrier is a histidine solution.

13. The method according to claim 1, wherein said eluant contacted with the carrier is an acidic solution of pH 1-6.

14. The method according to claim 1, wherein said chelating residue is a biscarboxymethylamino group, said metal ion is $Zn^{++}$ and said eluant contacted by the carrier is an acidic solution of pH 1-6.

* * * * *